US008861830B2

(12) United States Patent
Brada et al.

(10) Patent No.: US 8,861,830 B2
(45) Date of Patent: Oct. 14, 2014

(54) METHOD AND SYSTEM FOR DETECTING AND ANALYZING HEART MECHANICS

(75) Inventors: Rafael Brada, Hod Hasharon (IL); Michael Zarkh, Givat Shmuel (IL)

(73) Assignee: Paieon Inc. NY (US)

(*) Notice: Subject to any disclaimer, the term of this patent is extended or adjusted under 35 U.S.C. 154(b) by 330 days.

(21) Appl. No.: 13/290,155

(22) Filed: Nov. 7, 2011

(65) Prior Publication Data

US 2013/0116739 A1 May 9, 2013

(51) Int. Cl.
*G06K 9/00* (2006.01)
*A61B 6/00* (2006.01)
*A61B 5/05* (2006.01)

(52) U.S. Cl.
CPC .............. *A61B 6/503* (2013.01); *A61B 6/5217* (2013.01); *A61B 6/504* (2013.01); *A61B 6/486* (2013.01)
USPC ............................ 382/132; 382/256; 600/425

(58) Field of Classification Search
CPC .................................. A61B 5/02; G60K 9/00
USPC ......... 382/100, 103, 106–107, 128–134, 154, 382/162, 168, 173, 181, 232, 254, 274, 276, 382/285, 305, 312, 256; 600/428, 425, 450, 600/447
See application file for complete search history.

(56) References Cited

U.S. PATENT DOCUMENTS

| | | | |
|---|---|---|---|
| 5,722,405 A | 3/1998 | Goldberg | |
| 6,694,166 B2 | 2/2004 | Salome et al. | |
| 6,757,423 B1 | 6/2004 | Amini | |
| 7,041,061 B2 | 5/2006 | Kramer et al. | |
| 7,043,063 B1 | 5/2006 | Noble et al. | |
| 7,308,297 B2 | 12/2007 | Reddy et al. | |
| 7,577,281 B2 | 8/2009 | Nishiura | |
| 7,613,500 B2 | 11/2009 | Vass et al. | |
| 7,620,447 B2 | 11/2009 | Harel et al. | |
| 7,869,854 B2 | 1/2011 | Shachar et al. | |
| 7,890,169 B2 | 2/2011 | Ding et al. | |
| 7,904,155 B2 | 3/2011 | Yu et al. | |
| 7,907,764 B2 | 3/2011 | Matsuoka | |
| 7,951,083 B2 | 5/2011 | Sui et al. | |
| 8,145,293 B2* | 3/2012 | Zhang et al. ................... | 600/428 |
| 8,290,228 B2* | 10/2012 | Cohen et al. .................. | 382/128 |
| 2003/0167009 A1 | 9/2003 | Callahan | |
| 2005/0041769 A1 | 2/2005 | Launay | |
| 2007/0055142 A1* | 3/2007 | Webler ........................... | 600/425 |
| 2007/0197907 A1 | 8/2007 | Bruder et al. | |
| 2008/0242976 A1 | 10/2008 | Robertson et al. | |
| 2008/0255629 A1 | 10/2008 | Jenson et al. | |

(Continued)

FOREIGN PATENT DOCUMENTS

| | | |
|---|---|---|
| CN | 100577104 | 3/2008 |
| EP | 1998287 | 12/2008 |
| NL | 1016723 | 5/2002 |
| WO | 2009007910 | 1/2009 |

*Primary Examiner* — Seyed Azarian
(74) *Attorney, Agent, or Firm* — Soroker-Agmon (57) ABSTRACT

Method and apparatus for detecting and analyzing heart mechanical activity at a region of interest of a patient's heart are provided. The method comprises acquiring a time sequence of 2-dimensional X-ray images of a region of interest over at least part of a cardiac cycle; detecting coronary vessels in the X-ray images; tracking the coronary vessels through the sequence of images to identify movements of the coronary vessels; and analyzing the movements of the coronary vessels to quantify at least one parameter characterizing heart wall motion in the region of interest.

36 Claims, 5 Drawing Sheets

(56) References Cited

U.S. PATENT DOCUMENTS

| | | |
|---|---|---|
| 2010/0074487 A1 | 3/2010 | Miyamoto et al. |
| 2010/0189337 A1 | 7/2010 | Jandt et al. |
| 2010/0208957 A1* | 8/2010 | Chen et al. ............... 382/128 |
| 2011/0044524 A1* | 2/2011 | Wang et al. ............... 382/131 |
| 2011/0052035 A1 | 3/2011 | Kirchberg |
| 2011/0092809 A1 | 4/2011 | Nguyen et al. |

* cited by examiner

METHOD AND SYSTEM FOR DETECTING AND ANALYZING HEART MECHANICS

FIELD OF THE INVENTION

The present invention generally relates to cardiology procedures and more particularly to detection and analysis of heart mechanical activity.

BACKGROUND OF THE INVENTION

Information regarding the mechanical activity of the heart may be of interest for both diagnosis and treatment of heart diseases. Such information may be useful for early diagnosis of a cardiac disease, for assessing a disease severity and for facilitating decision and planning regarding possible treatment.

In particular, information regarding the mechanical activity at different regions of the heart may be useful for various applications. For example, in applications such as artificial pacemaker implantation, particularly in the case of a biventricular pacing, it is advantageous to map the local mechanical activity of a patient's heart in order to determine optimal position for lead implantation. Artificial pacing provides electrical stimuli for causing cardiac contraction when the intrinsic myocardial electrical activity is impaired. A pacing system consists of a pulse generator and insulated electrode leads which carry the electrical impulses from the generator to the heart. The pulse generator is typically placed subcutaneously or submuscularly in the chest wall while the insulated leads are inserted transvenously to be attached to the heart. The procedure is typically facilitated by fluoroscopy which enables the physician or cardiologist to view the passage of the electrode lead. At the tip of each lead is an electrode, or several electrodes, that deliver the necessary electrical impulses to the specific location of the tip. The success of the pacing therapy depends to a great extent on the specific locations of the implanted leads, particularly in the case of a biventricular pacing.

A biventricular pacing, also known as cardiac resynchronization therapy (CRT), is an interventional procedure in which both the right ventricle (RV) and left ventricle (LV) of the heart are stimulated synchronously to improve the heart pumping efficiency. About 20 to 30 percent of patients with heart failure suffer from desynchronized contraction of the right and left ventricles (desynchrony) and need a biventricular pacing for pacing both sides of the heart to restore synchrony. While a standard pacemaker typically has two leads for stimulating the right ventricle and the right atrium, a biventricular pacemaker has an additional lead for pacing the left ventricle. As with a standard pacemaker, the first and the second wires are threaded through the veins to the right ventricle and to the right atrium, usually through the sub-clavian vein and/or cephalic vein, which are relatively easily accessed from the pocket under the skin. In a bi-ventricular pacemaker, a third wire is implanted in order to stimulate left ventricular wall contraction, in a more complicated procedure. The third wire passes through the right atrium into the coronary sinus (CS) and then placed through one of the CS branches to pace the left ventricle. The location of the implanted lead in the left ventricle is very crucial to the therapy efficiency. Indeed, about 30 percent of the time following a CRT implant the patient does not respond to the therapy (non-responders). A possible way to improve the response rate may be by placing the lead for pacing the left ventricle in the area that contracts last. Thus, a proper application of a biventricular pacing therapy would require detailed knowledge of the temporal and spatial characteristics of LV contraction on a patient-by-patient basis. Useful information may also be gained from comparing the temporal-spatial distributions of the mechanical and electrical activations. Such comparison may indicate whether the cause of dysfunction at a specific location is a defect in the heart's electrical conduction system or a scarred tissue. For example, if both electrical and mechanical activation are delayed with a similar latency, the problem is most likely in the electrical conductivity. In such a case, external pacing can improve synchronization of contraction. However, if the delay in mechanical activation is significantly longer than the delay in electrical activation, the problem is probably caused by mechanical injury of the tissue.

The CRT application is only an example of a cardiac procedure to which the invention is directed. Another exemplary cardiac procedure anticipated by the invention, for which an analysis of regional mechanical activity of the heart may be beneficial, is the investigation of coronary arteries. Narrowing of coronary arteries, i.e., a stenosis, can lead to reduced blood flow to a heart muscle, angina, and eventually to a heart attack. It is therefore important to identify stenotic arteries and to assess stenosis severity in order to decide if and which interventional treatment is required (e.g., balloon angioplasty and/or deployment of stents). Typically, the severity of the stenosis is determined by assessing the extent of the artery narrowing or by measuring blood pressure and flow gradient between proximal and distal parts of disease using FFR (Fractional flow reserve) techniques. Analysis of the regional or local mechanical activity of the heart, as provided by the present invention, and in particular assessing the extent of contractility of the wall at the region distal to the stenosis, may facilitate assessing of a stenosis severity. Similarly, analysis of the local mechanical activity of the heart may facilitate identification of necrosis and infarct areas.

A variety of volumetric imaging systems are presently available, such as ultrasound, computed tomography (CT) and magnetic resonance, which provide time-sequence volumetric data that may be analyzed to obtain spatial-temporal information of the heart mechanics. However, volumetric imaging modalities require expensive equipment which is not widespread and therefore are not conducted for all patients. Additionally, these systems are generally adapted for diagnosis and for planning interventional procedures but are not configured for real-time imaging during such procedures. On the other hand two-dimensional (2D) X-ray imaging methods by conventional fluoroscopy apparatus, such as a C-arm X-ray system, are routine diagnostic methods in most cardiology clinics and are typically deployed during interventional procedure, such as implantation of a pacemaker or a stent, to allow navigating and location the device.

There is therefore a need for a method and system for analyzing the mechanical activity of the heart in general, and of mapping local heart motion in particular, by using standard, widespread imaging equipment, such as fluoroscopy X-ray machine, which is available in most heart physiology and cardiology clinics.

SUMMARY OF THE INVENTION

The present invention provides method and system for analyzing and quantifying heart motion. Specifically, some embodiments of the present invention present methods and systems for motion analysis of the heart mechanical activity by analyzing a time sequences (and in some embodiments, two or more time sequences) of 2-dimensional (2D) X-ray images of coronary vessels through the cardiac cycle. In particular, embodiments of the invention provide for quantifying one or more parameters that characterize local heart motion at a region of interest, including the degree and timing of local contraction.

One aspect of the present invention is a method for detecting and analyzing heart mechanical activity at a region of interest of a patient's heart. The method may comprise: acquiring a time sequence of 2-dimensional X-ray images of a region of interest over at least part of a cardiac cycle; detecting coronary vessels in said X-ray images; tracking the coronary vessels through said sequence of images to identify movements of the coronary vessels; and analyzing the movements of the coronary vessels to quantify at least one parameter which characterizing heart wall motion in the region of interest. The X-ray images may be angiograms obtained by injection of a contrast agent, or images of a radiopaque device inserted through the coronary vessels, or a combination thereof. The coronary vessels may be coronary veins and/or coronary arteries. The parameter characterizing the motion may relate to one or more of the following: the magnitude (or degree) of contraction, the timing of contraction, magnitude of displacement and timing of displacement. In accordance with certain embodiments, the parameter is the timing of at least one of the following: start of contraction; end of contraction; and maximal velocity of contraction. The part of the cardiac cycle may be a systole.

In accordance with some embodiments, analyzing may include decomposing the movements of the vessels into a strain component and a non-strain component and/or quantifying at least one of a strain component of the motion and a displacement component of the motion.

The method may further include a step of generating a strain graph which represents the contraction or expansion, or both contraction and expansion, through at least part of the cardiac cycle. Timing may be derived from the strain graph by various methods, including a curve fitting technique.

Tracking the coronary vessels may be performed by calculating local transformations of the coronary vessels through the time sequence of images or by selecting and tracking a plurality of control points in the coronary vessels through the time sequence of images, or by a combination thereof. In accordance with some embodiments, the local transformations may be decomposed into a strain component and a non-strain component and the strain graph may be calculated using the scale factors that are obtained by the local transformations. Yet, in accordance with other embodiments, the strain graph may be measured as a change in time of the root mean squares, or of weighted root mean squares, of the distances between control points to the mass center of said control points, or as the change in time of weighted average distances between the control points.

In accordance with some embodiments, the region of interest may be divided into segments wherein the vessel motion in each segment may be analyzed separately for generating and optionally displaying a motion map which presents the spatial distribution of motion over the region of interest. The motion map may present one or more parameters characterizing the motion, including the timing of contraction. The method may further comprise a step of identifying the last to contract segment.

The method may also include a step of applying an electrical activation in one or more locations in patient's heart wherein the sequence of the X-ray images is acquired in response to the electrical activation. In accordance with some embodiments, the method may also include comparison of the electrical and mechanical activities at one or more locations in the region of interest. The electrical activity may be intrinsic or responsive to electrical excitation.

The method may also include a step of identifying a location for treatment and/or assessing severity of a disease based on the motion map. In accordance with specific embodiments of the invention, the region of interest is the left ventricle and the method further comprises a step of selecting a location for implanting a left ventricle pacing lead. Yet, in accordance with other specific embodiments of the invention, the at least one parameter is contractility and the method further comprises a step of detecting a scar tissue based on the quantification of the contractility.

The method may further include a step of selecting a projection direction for acquiring the time sequence of images. The projection direction may be an orthogonal view to the heart's surface at the region of interest or an orthogonal view to rotational motion of the heart at the region of interest. In accordance with some embodiments, the projection direction may be derived from a 3D model of the coronary vessels. The 3D model may be reconstructed from two angiograms taken from different perspectives.

In accordance with some embodiments, two or more time sequences of X-ray images of the region of interest are acquired under different projection directions and the quantifying of the at least one parameter is made by using the analysis results obtained from analyzing each of the two or more time sequences separately. The motion maps obtained from the analysis of the two or more time sequences may be consolidated into a single motion map.

Another aspect of the invention is an apparatus for heart motion analysis. The apparatus includes an image acquisition unit for receiving one or more time sequences of X-ray images which expose coronary vessels and a processor configured with one or more applications programs comprising computer instructions for one or more of the following: identifying and tracking the coronary vessels through said one or more time sequences of images; identifying movements of coronary vessels through at least part of a cardiac cycle; analyzing and quantification of motion of at least one region of heart; and generating local strain graphs and/or motion maps. The apparatus may further include a projection direction selecting unit for selecting a projection direction for capturing the one or more time sequences of X-ray images. The apparatus may further include a display unit for displaying analysis results, including strain graphs and motion maps.

Yet, a further aspect of the invention is a non-transitory computer readable storage medium containing a set of instructions for a general purpose computer. The set of instructions may comprise one or more of the following: receiving a time sequence of 2-dimensional X-ray images of showing a region of interest over at least part of a cardiac cycle; detecting coronary vessels in said X-ray images; tracking the coronary vessels through said sequence of images to identify movements of the coronary vessels; analyzing the movements of said coronary vessels to obtain at least one parameter characterizing heart wall motion in said region of interest.

Other embodiments, as well as objects and advantages of the present invention will become apparent from the following detailed description.

DETAILED DESCRIPTION OF THE INVENTION

The present invention provides method and system for heart motion analysis by analyzing and quantifying the motion of coronary vessels using one or more time sequences of 2-dimensional X-ray images of a region of the heart, each of the time sequences is acquired under a selected projection angle. The invention is based on the realization that the motion of coronary vessels reflects the motion of the heart wall. Thus, detecting and analyzing the motion of the coronary vessels in a defined region of the heart wall, over at least part of the cardiac cycle, will provide information about the heart mechanical activity in the defined region. In particular, the invention provides for mapping the heart mechanical activity over a region of interest by quantifying the motion of the heart wall at different locations in the region, thus allowing comparison between the mechanical activity at the different locations and for selecting a specific location according to a desired criteria, e.g., location last to contract, location of maximum or minimum contraction etc.

The invention may be deployed at a diagnostic stage for assessing severity of a disease and for facilitating planning and optimizing of an interventional procedure, such as an implantation of an intravascular device, when required. As mentioned above, implantation of an intravascular device is typically carried out under conventional fluoroscopy to enable the physician to view the passage of the device through the vessels. As the present invention provides for using the same equipment and setting which is typically used during the interventional procedure, it enabling providing analysis results regarding immediately before, or even during the interventional procedure.

Embodiments of the invention are particularly suitable for, but are not limited to, analyzing the spatial and temporal distribution of contraction motion of the left ventricle in order to identify an optimal location for placing a lead of a biventricular pacemaker.

Generally, the local 3D motion of the heart wall can be decomposed into two components: the first component expresses change of distances between neighboring points and is referenced as a strain (contraction, when distances decrease or expansion, when distances increase); the second non-strain component does not involve change of distances between neighboring points and consists of translation and/or rotation. Strain may be anisotropic. Specifically, one can differentiate between a circumferential strain when cross sections (segments) perpendicular to the long axis of a heart chamber change length and between a longitudinal strain when lines substantially parallel to long axis change length. The present invention is particularly directed at quantifying and mapping the strain component. It will be realized that at a projection direction perpendicular to the heart wall surface, contraction and expansion are visualized as a change in scale of the vessel tree, or in other words, as a change of distance between points, while rotation and translation are visualized without change of distances.

Figure 1:
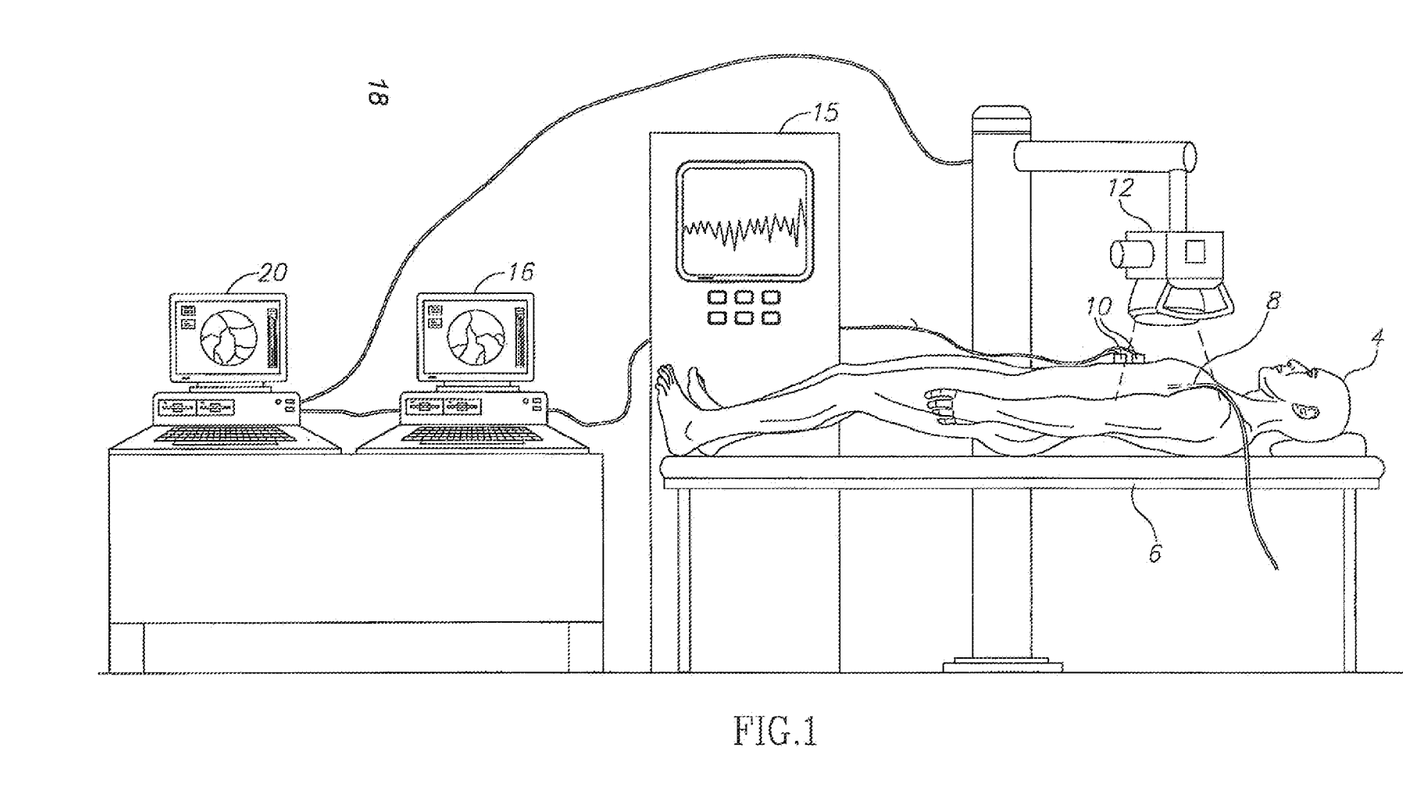
FIG. 1 is an illustration of an exemplary setting in which the proposed invention may be deployed.

Referring now to the drawings, FIG. 1 depicts an exemplary setting in which the present invention may be deployed. As shown, a patient subject 4 is lying on a bed 6 in an electrophysiology clinic or an operation room. A computerized X-ray machine 12, directed at the patient's heart, is activated to produce a time sequence of X-ray images of the heart area at the field of view. Preferably, machine 12 is a CCD X-ray machine provided with a C-arm mechanism to allow adjusting the projection angle with respect to the patient's body. Machine 12 may be connected to and controlled by work station 18, which receives and optionally displays X-ray images from machine 12. In order to expose the coronary vessels at the heart area under view, the X-ray images are preferably obtained under angiography procedure by injecting contrast agent to the patient, as is well known in the art. Where the vessels to be detected are the coronary veins, the angiography is preferably carried out after a balloon is inserted and inflated inside the vein, e.g., the coronary sinus, so as to prevent the blood flow from dispersing the contrast agent before the images are taken. Alternatively, or additionally, the coronary vessels may be visualized by a radiopaque intravascular device, e.g., a catheter 8, a pacing lead, or the like, which conforms to the vessels shape. The setting optionally includes an ECG (electrocardiography) monitor 15, including electrodes 10 placed on the patient's chest. A work station 16 communicates with work station 18 to receive the image data and optionally may also communicate directly with monitor 15. Work station 16 is configured to receive the image data and may include the application programs and/or hardware for enabling the operation of the systems and methods of the embodiments of the invention for analyzing and quantifying motions of the patient's heart. Optionally, the setting may also include means for applying electrical excitations and/or for measuring electrical activity at different locations of the heart, for example by inserting an electrode lead (not shown) through catheter 8. This option allows for carrying out motion analysis in response to electrical excitation and/or for mapping the electrical activity of the region of interest and to display and compare motion activity and electrical activity maps. Accordingly, workstation 16 may be configured to receive and to analyze measurements and/or records of local electrical activity measurements. Preferably, work station 16 is a computing platform, such as a personal computer, a mainframe computer, or any other type of computing platform that is provisioned with a memory device (not shown), a CPU or microprocessor device (not shown), several I/O ports (not shown), input and output devices, such as a touch screen, a keyboard, a mouse and a display device, to enable a physician or another stuff member to view and/or manipulate the products of the applications. Alternatively, work station 16 delivers the output to another system via communication means. In an alternative embodiment, work station 16 can be a DSP chip (not shown), an ASIC device (not shown) storing the commands and data necessary to execute the methods of the present invention. The applications comprise a set of logically inter-related computer programs or computer components and associated data structures that interact to perform the invention.

Figure 2:
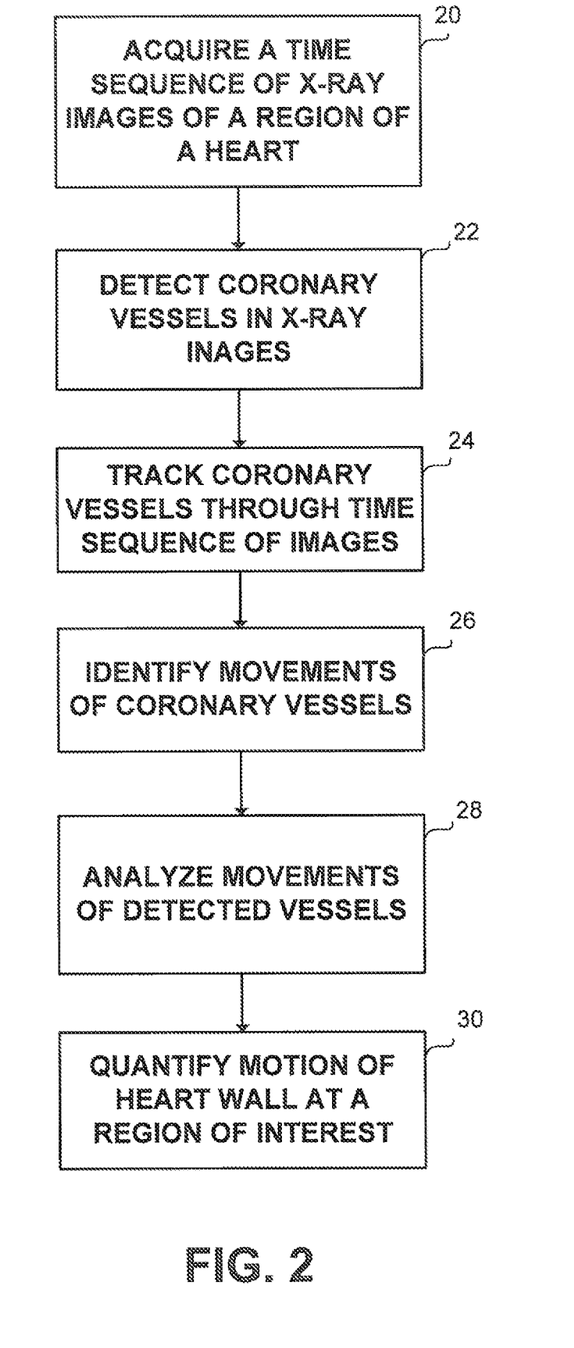
FIG. 2 is an overall flowchart of a method for analyzing heart mechanical activity in accordance with an embodiment of the invention.
Figure 3:
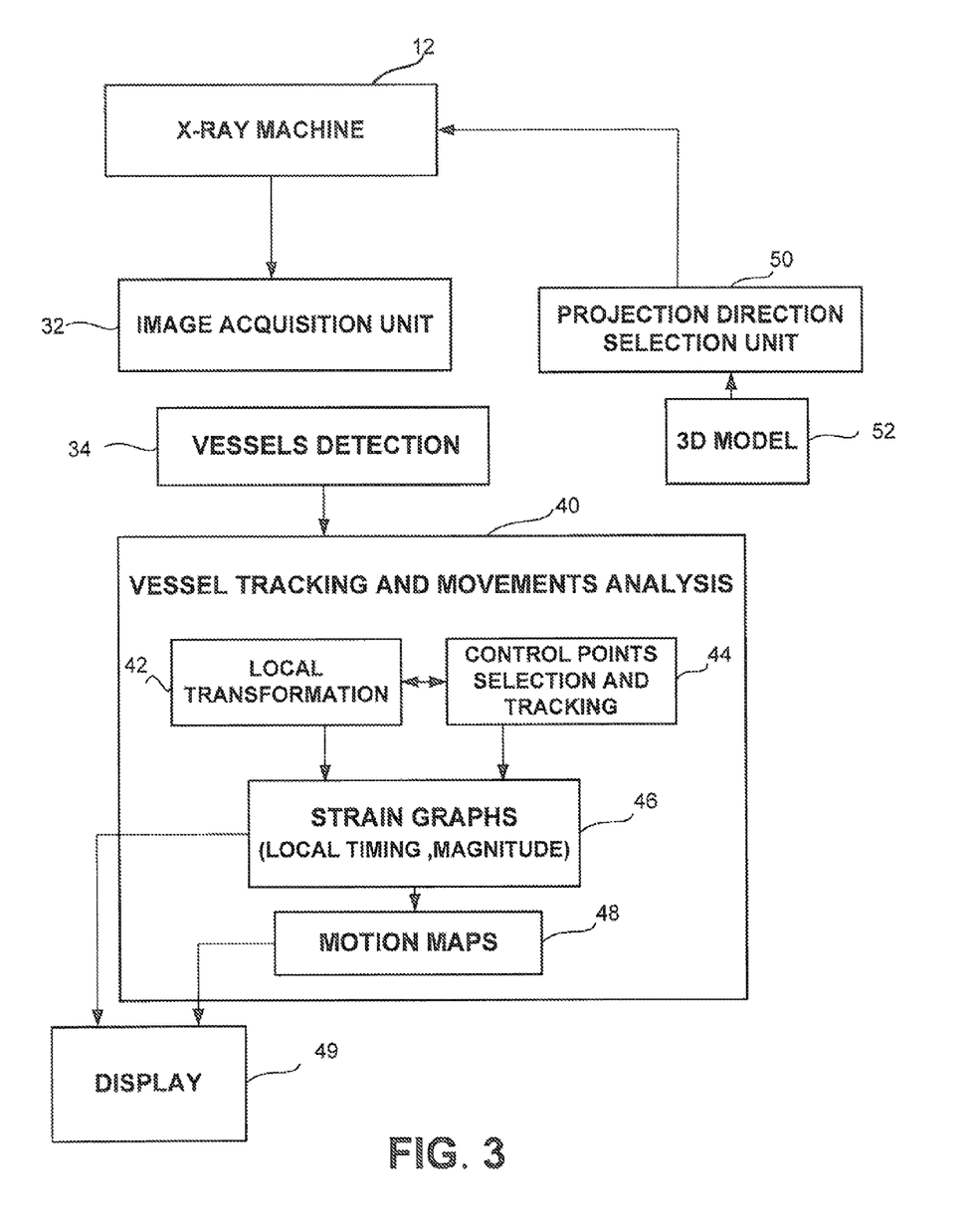
FIG. 3 is a block diagram of an apparatus for analyzing heart mechanical activity in accordance with an embodiment of the invention.

With reference to FIGS. 2 and 3, an exemplary embodiment of the invention will now be described. A more detailed discussion of some of the blocks in FIGS. 2 and 3 follows the overview description.

Beginning at step 20, a time sequence of 2-dimensional X-ray projection images captured by machine 12 of FIG. 1 is acquired and preferably stored by image acquisition unit 30. The 2-dimensional images are preferably angiograms taken after the patient has been injected with contrast agent. Alternatively, or additionally, the 2-dimensional images may be images of a radiopaque device inserted into the vessels. In that case, motion of radiopaque parts of device represent motion of the vessel and tracking the motion can be performed by tracking radiopaque parts of device. The time sequence comprises "snapshots" (i.e., angiographic cine-runs) of the coronary vessel under the same projection angle during at least part of the cardiac cycle of the patient. Preferably the projection direction is selected to be substantially orthogonal to the surface of the heart at the region of interest or to the main velocity component thereof. In accordance with some embodiments of the invention, two or more time sequences of images may be used for analyzing the motion in a region of interest wherein each time sequence is taken from a different projection direction, as explained in more detail below.

Next, at step 22, the coronary vessels at the region of interest may be detected. Detection of vessels is performed by component 34, for example by using DSA (Digital Subtraction Angiography) technique, namely by subtraction images taken before injection from the images taken after injection of the contrast agent. The augmented DSA should preferably be synchronized with heartbeat phase and compensated for breathing movement. The vessel detection step may further comprise high pass filters and vessel enhancement procedures as is well known in the art.

Next, at steps 24 and 26, after the vessels in the region of interest have been identified, the vessels are tracked through the time sequence of images by component 40 in order to identify the movements of the vessels through at least part of the cardiac cycle. In addition to exposition of vessel by injection of contrast solution, in a case when a device is inserted to the vessel, tracking the vessel can be performed also by tracking the opaque parts of device. Tracking the vessels through the time sequence of images may be performed by calculation of local area transformations from one frame to the next by module 42, or by tracking selected control points in the detected vessels, by module 44. Yet, in accordance with some embodiments of the invention, tracking the vessels may be performed by a hybrid combination of the two methods.

Following, in steps 28 and 30, the movements of the vessels at the region of interest are analyzed over at least part of the cardiac cycle to quantify the motion of the heart wall at the detected region. The motion of the heart wall can be quantified for the whole detected region, or the region may be divided into segments for quantifying motion in each of the segments separately. This way, the motion of the heart wall can be mapped over the region of interest. In particular, local strain graphs 46, which exhibit the change of strain through the cardiac cycle can be generated for each of the segments and the values of different parameters relating to timing of specific phases and/or to the magnitude of the strain can be derived from these graphs. The spatial distribution of the so obtained values can then be presented as motion maps 48 on a display device 49. Alternatively or additionally, motion maps 48 may be derived from displacement graphs. Motion maps 48 enable comparison between different locations with respect to timing and magnitude of strain, in particular with respect to time and magnitude of contraction, and allow for determining which location is most suitable for a particular application. For example, where the region of interest is the left ventricle, comparison of the strain graphs allows for selecting the last to contract location. Similarly, locations of necrotic tissues can be identified as locations of low contractility.

Tracking of Vessels and Creation of Strain Graphs

Tracking the coronary vessels through the time sequence of images for identifying and quantifying their motions at a region of interest can be performed by two main approaches.

The first approach is based on estimation of local area transformations from one frame to the next using known methods such as optical flow methods, and in particular the Lucas-Kanade method, for estimation of affine transformation. Affine transformation can be decomposed into translation, rotation and scale change in two directions, described by two scale factors. The strain factor can be defined for example as the minimum of the two scale factors. The local strain at a time $t_k$ can be defined as the cumulative product of strain factors relating to the sequenced transitions from frame 1 to frame k:

$$S_N(t_k) = \Pi_{i=1}^{k-1} s(t_i, t_{i+1}), \quad (1)$$

Where $s(t_i, t_{i+1})$ is a local strain factor of transition from frame i to frame i+1.

A general transformation, more complex than affine transformation, can be reduced to affine transformation for example by sampling on a grid of points and estimation of affine coefficients as a least square solution. Alternatively, sampling on a grid can be input to the second approach of tracking the vessels, described in the following.

Figure 4:
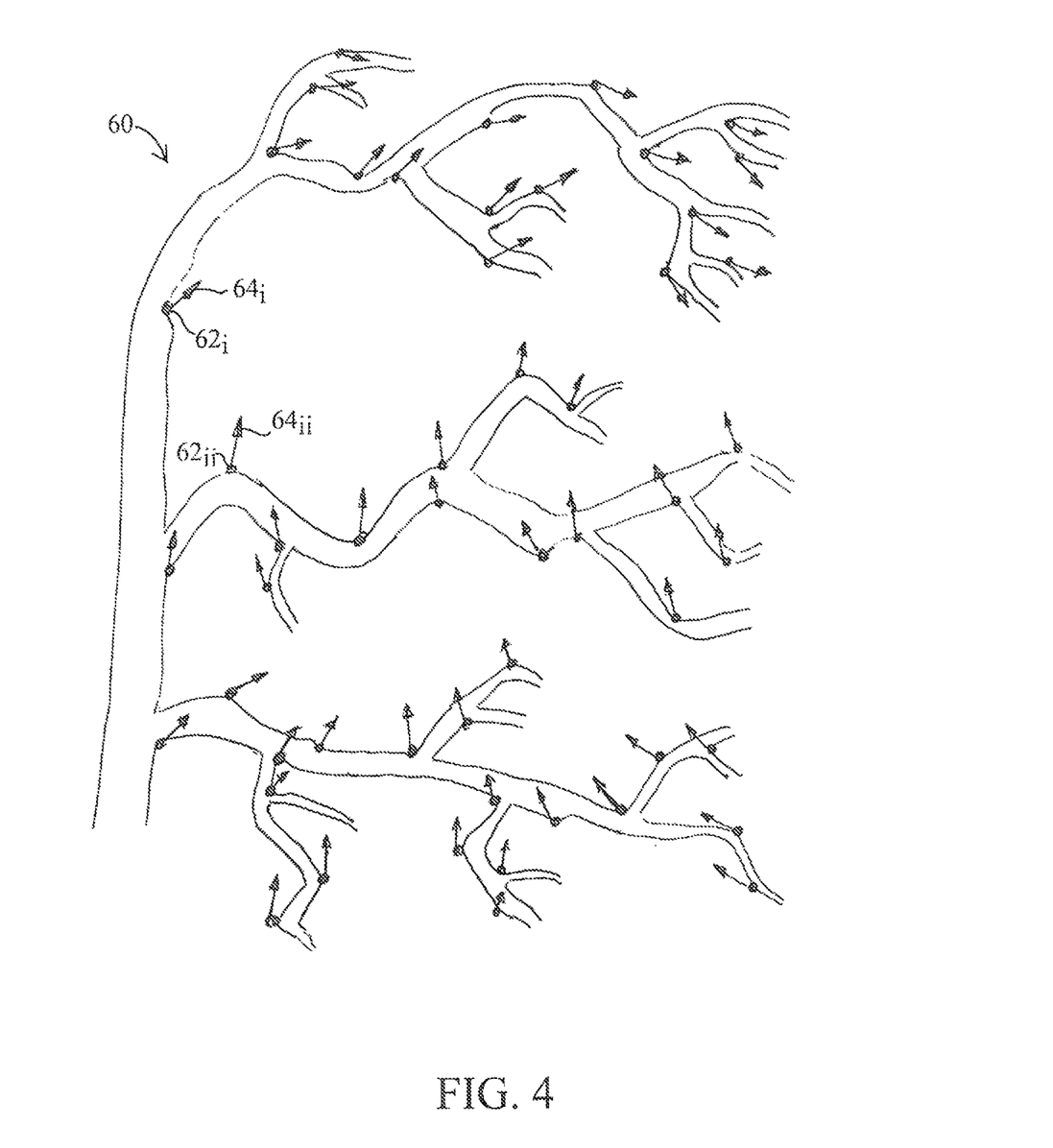
FIG. 4 is a schematic illustration of a coronary vessel showing selected control points on the vessel and their displacements between two instances of time.

The second approach is based on choosing a set of control points (landmarks) CP on the detected imaged coronary vessels and creating tracks of the chosen control points as a time sequences through heart cycle. The criterion for choosing control points is their uniqueness. For example, such distinctive points may be branching points, points with maximal local curvature, points of sharp change of vessel radius and the like. FIG. 4 depicts an exemplary vessel tree 60 and a plurality of selected control points 62 denoted by blackened points. Possible movements of control points 62 are indicated by arrows 64. Selection of the control points may be automatic or semi-automatic procedure.

Having established the tracks of control points $CP_i(t_k)$, i=1, ..., N, a strain measure can be defined for example as the average distance between control points CP:

$$S(t_k) = (\Sigma_{i,j \in G} |CP_i(t_k) - CP_j(t_k)|)/N \quad (2)$$

where G defines any subset of control points. In particular, subsets of CP can be selected per vessel or part of a vessel. Alternatively, the strain measure $S(t_k)$ can be defined as the average distance (root mean square distance) of the control to the mass center of the group of points belonging to subset G.

A weighted version of equation (2) may be used:

$$S(t_k) = (\Sigma_{i,j \in G} w_i w_j |CP_i(t_k) - CP_j(t_k)|)/(N(\Sigma w_i)^2), \quad (3)$$

where the weights $w_i$ may be selected to determine local estimation of strain in a neighborhood of a given point p. In this case the weights may be defined as:

$$w_i = F(|CP_i(t_0) - p|) \quad (4)$$

with function F being for example $F(z) = e^{-\sigma z}$, where σ represents the degree of locality.

Alternatively, or additionally, the Weights may represent the degree of confidence or uniqueness of every control point.

Strain $S_N(t_k)$ is defined as the normalized change of distances, namely the value of strain measure $S(t_k)$ obtained by equations (1), (2) or (3) divided by the maximal value of strain measure $\max_k S(t_k)$. For every frame k: $S_N(t_k) = S(t_k)/\max_k S(t_k)$.

The contraction percent (or contractility) is defined as:

$$C_N = (1 - \min_k S(t_k)) * 100. \quad (5)$$

When the vessel skeleton tree is explicitly extracted from the image, for example at time $t_0$, a strain graph can be calculated using formula (3) for every point of the skeleton for a chosen degree of locality σ, where G represent control points associated with a given vessel (or set of neighboring vessels. Indeed, if a particular point of a specific skeleton branch is used as point p in (4) and a subset of control points related to this branch (and optionally to all or part of its children branches) is used as set G in (3), the strain graph is defined for point p. Doing so for all possible points of a vein tree, a strain graphs for the whole vessel tree can be obtained.

A modification of equation (3) can be used:

$$S(t_k) = (\Sigma_{i,j \in G} w_i w_j |CP_i(t_k) - Pref|)/(N(\Sigma w_i)^2), \quad (6)$$

where Pref is some reference point.

In particular, if $Pref = \Sigma_{i \in G} w_i CP_i(t_k)/\Sigma_{i \in G} w_i$ then Pref is the mass center of group of points of subset G.

If $Pref = \Sigma w_i CP_i(t_k)/\Sigma w_i$ then Pref is the global mass center.

It will be appreciated that the first and second approaches may be combined in a hybrid algorithmic scheme. For example, tracks of CPs can be performed by calculation of local transformations. On the other hand, a local transformation can be expressed as correspondences of points (CPs) of a given grid in a way the tracks of "CPs" are created through heart cycle and then processed as if they were obtained by tracking of control points.

In some cases, estimation of the local motion as a sequence of displacements (displacement motion) through consequent frames may be of interest. For example, displacement of a point (or of the mass center of a group of points) relative to its diastolic location as function of time may substitute contraction graph in alternative, consequent or complimentary analysis. In this case, Pref in equation (6) can be taken as:

$$Pref = CP_i(t_0) \quad (7)$$

For G consisting of a single point, equation (6) expresses displacement of this point. For a general subset G, equation (6) is the average displacement of the group of points belonging to G.

Definition of Contraction Timing

Figure 5:
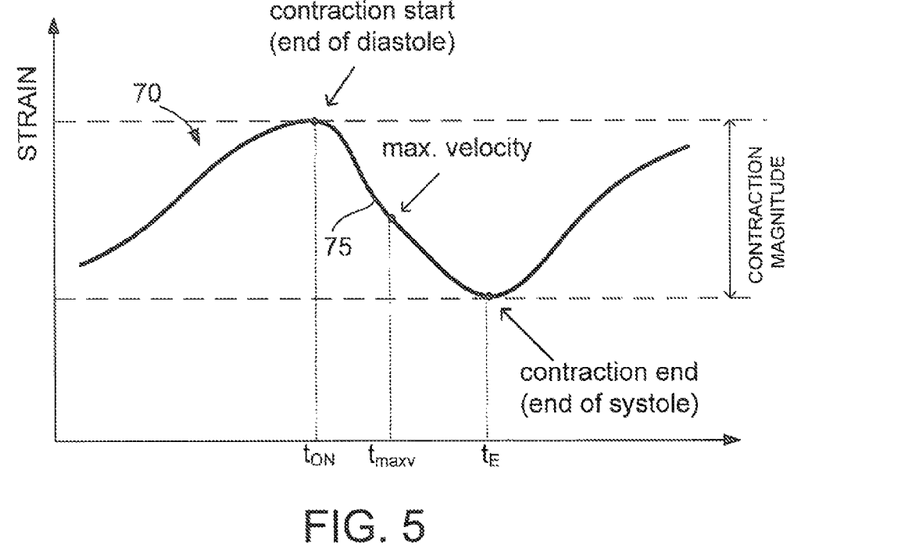
FIG. 5 is a schematic presentation of a strain graph.

FIG. 5 is a schematic representation of a strain graph 70 showing the change of local strain through the cardiac cycle. The systolic contraction is represented in the graph by decreasing slope 75 starting at a maximum point (end diastolic point) and ending at a minimum point (end systolic point). The different contraction phases, for example the onset of contraction, the maximal velocity of contraction and the end of contraction, may be of clinical interest when comparing contraction at different locations of the heart. Accordingly, different parameters can be defined for characterizing the contraction timing, including contraction onset ($t_{ON}$), contraction end ($t_E$) and timing of maximal contraction velocity ($t_{max,v}$). From calculation point of view, evaluation of different timing parameters can have different robustness to noise and aspect angles.

Different methods may be used for deriving the contraction timing parameters from the strain graphs. One optional method is based on a technique of curve fitting, for example a sinus fit which consists of choosing the phase, amplitude and period of a sinus in order to best fit to the strain graph data points. In that case onset, end and maximal velocity of contraction can be defined as the maximum, minimum and middle point between maximum and minimum of the best fitting sinus. Another fit option is a straight regression line fit. In this case, the onset and end of contraction can be defined as the points of intercept of the found regression line with the values max(S) and min(S), respectively, and the maximum velocity point can be defined as the halfway between the two. Alternatively, the maximum velocity point can be defined as the center of mass of the data points of the strain graph which support the regression line, where the mass (or measure of support) can be defined as the absolute difference between a strain value and a regression value.

Another optional method for finding the maximal velocity, not by using a fit approach, may be by using smoothing procedures for smoothing the strain graph and finding the point of maximal negative velocity. The amount of smoothing is preferably of the order of the systole length.

It will be appreciated that the above described methods for extracting timing parameters from strain graphs are only non-limiting examples and that other methods may be used as well.

Regardless of the specific method used for timing extraction from the strain graphs, the results may be supplemented by a confidence measure expressing the quality of fit and/or other characteristics of the graph. The quality of the fit can be evaluated, for example, as the integral of the residuals or the number of data points which well supports the fitted curve.

Heart Mechanical Activity Maps

Local timing measurements can be presented to the user as color coded map (Motion Map) over a 2D or 3D model of the heart surface, and in particular over a model of the vessel skeleton. The timing values presented by the color code may be relative to an arbitrary chosen time or relative to a specific trigger, for example R-peak in the ECG signal. The last option is essential in consolidation of 2 or more motion maps when R-peak may serve as synchronization instant. The last to contract location may be marked with special mark and suggested as deployment site. Motion map may incorporate additional information layers, for example local reliability of measurements, (or not presenting results in regions with low reliability), scar tissue mapping, favorable projection direction for regions with low reliability, etc. Electrical activity timing map can be presented in parallel with or as an additional layer of a motion map.

Electrical Activation Map vs. Motion Map

As mentioned above, comparison of electrical activation time and mechanical activation time in different locations has a particular interest because it can point to different source of pathology. For example, if in some location both electrical and mechanical activation are delayed with similar latency the problem is most likely in electrical conductivity, for example due to left bundle branch block (LBBB) or right bundle branch block (RBBB). In such situations external pacing can improve synchronization of contraction. Another situation is when electrical activation occurs with normal delay and mechanical activation comes significantly later. In such a case, late mechanical activation is probably caused by mechanical injury of the tissue (scar). International publication WO2006117773, the content of which is incorporated herein by reference, discloses a method for selecting a location for implanting a biventricular pacing lead which is based on mapping the electrical activity of the left ventricular. The present invention provides for comparing a mechanical activity map of a region of interest obtained by the method of the present invention with an electrical activity obtained for example by the method described in WO2006117773.

In accordance with some embodiments of the invention, the heart mechanical activity analysis and the generation of strain graph may be performed based on both intrinsic regional activity and in conjunction to the application of electrical stimulation at different locations of the heart, not necessarily at the region undergoing the mechanical activity analysis. For example, electrical excitation may be applied at the right ventricle via an RV lead and mechanical and electrical response may be measured at different locations in left ventricle wall.

Scar Tissue Detection

In accordance with some embodiments of the invention, a scar tissue can be detected by using the strain measurement. If the contraction percent C in equation (5) is small for some region and a non-contractile movement of that region starts later than motion of surrounding regions then the region is likely to be a scar region. In addition relative latency between electrical activation of the region and its mechanical activation can increase probability of scar tissue.

2D Observed Strain Versus True 3D Strain

Figure 6:
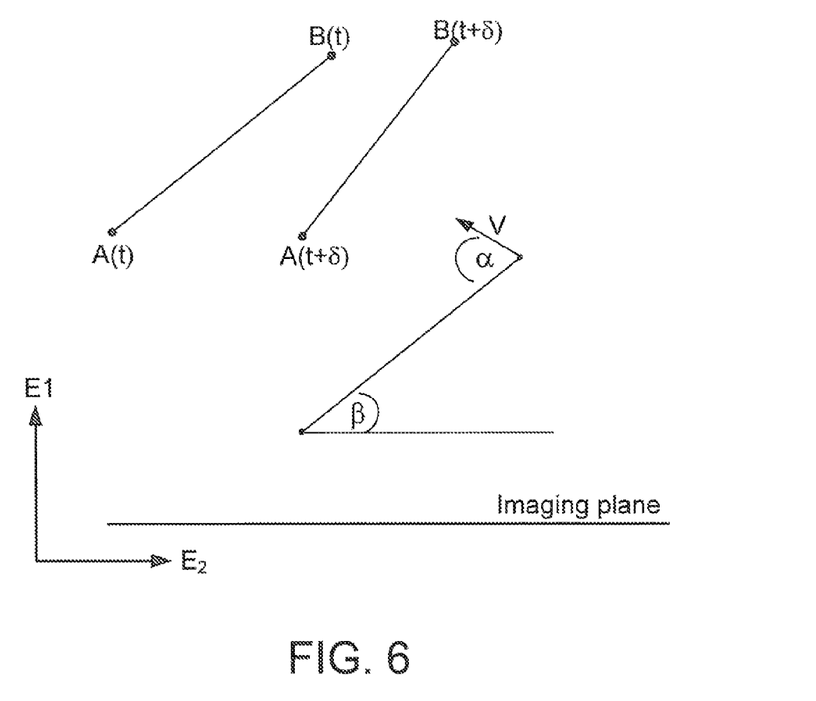
FIG. 6 is a schematic illustration demonstrating 3D movement of a segment in relation to an observation (imaging) plane.

The following analysis determines conditions for accurate measurement of strain in 2D in comparison to true 3D strain. An elementary strain measurement involves tracking of change in time of the distance between two points. Consider an infinitesimal setting of the analysis. Let A(t),B(t) be two neighboring 3D points on the heart pericardium at instant t and A(t+δ),B(t+δ) be their location at instant t+δ. Let E be an observation vector, perpendicular to imaging plane (C-arm orientation). Generally, motion of a segment AB can be decomposed into shift (translation), rotation and scale change. Strain is indifferent to shift. Rotation and scaling occurring in imaging plane are observed properly. The problem is a situation when rotation and scaling take place in out of imaging plane and are mixed up when projected into the image. In such a situation, the scaling measure in 2D may be inaccurate. In order to evaluate distortion of 2D strain measurements and understand in what conditions the measurements accurately reflect the real 3D strain, consider the motion of the segments in a coordinate system defined by the view vector and the segment direction. Let $(E_1, E_2, E_3)$ be an orthonormal basis defined by three vectors: the first is view vector $E_1=E$, the second $E_2$ is projection of vector $\overrightarrow{AB}$ on the imaging plane (plane orthogonal to E) and the third $E_3$ is orthogonal complement of the first and the second (their cross product). The 3D motion of the segment AB can be decomposed in two motions in imaging plane $E_2, E_3$ and in "out of plane" motion in $E_1, E_2$. As mentioned above the "in plane motion" does not introduce any distortions in strain observation. The "out of plane" motion mixes rotation and strain and is manifested in image as a strain only (shortening or enlargement of distance between points on axis $E_2$). FIG. 6 illustrates the situation, where A(t),B(t) and A(t+δ),B(t+δ) are projections of A(t),B(t) and A(t+δ),B(t+δ) into the plane $E_1, E_2$, and V:

$$V=B(t+\delta)-(B(t)+A(t+\delta)-A(t))$$

is the displacement vector of the point B relative to point A, α is angle between segment and displacement vector, β is angle between segment AB(t) and the imaging plane.

In a first approximation the 3D strain is:

$$S_{3D}=V\cos\alpha/|AB(t)|$$

while the strain observed in 2D is:

$$S_{2D}=V\cos(\alpha-\beta)/(|AB(t)|*\cos\beta)$$

The ratio between the 2D to the 3D strain is $$\frac{S_{2D}}{S_{3D}} = \frac{\cos(\alpha-\beta)}{\cos\alpha\cos\beta} = 1 + \tan\alpha\tan\beta \tag{8}$$

The conclusion from (8) is that the error in evaluation of the strain in the 'out of plane' motion is proportional to the value:

$$\tan\alpha\tan\beta$$

meaning that the 2D strain measurement is substantially accurate when the 'out of plane' motion is close to pure contraction or expansion ($\alpha \approx 0$) or that the segment is orthogonal to the view vector ($\beta \approx 0$). Thus, a sufficient condition for accurate strain measurement in 2D is orthogonality of the projection direction to the observed vessels.

Selecting Optimal Projection

A practical implication of the above conclusion might be a method of optimization of number and orientation of C-arm projections for good coverage of vessels of interest. The optimization, carried out by component 50 in FIG. 3, can be performed for a specific patient if his/her coronary tree 3D model is available. Another optimization can be carried out for a population.

Different types of optimization methods may be incorporated into the procedure adjusting workflow and improving diagnostic accuracy of the suggested method.

The first group of suggested optimization methods assumes existence of 3D model (52 in FIG. 3) of coronary tree or subset of segments of coronary tree. The 3D model can be reconstructed from existing angiographic projections acquired during the procedure, for example by the methods disclosed in international publications WO0185030 and WO2005031035, the full content of which is incorporated herein by reference, or can be imported from other modalities acquired prior to procedure (e.g., CT, MRI).

Let $M=(M_1, M_2, \ldots, M_N)$ be a set of 3D vessel segments building up the 3D model. The first simple type of projection optimization to choose a projection direction E is by solving minimization problem:

$$D_{min}=\min_v\{\max_i D(E, M_i)\} \tag{9}$$

where D (E, $M_i$) is deviation in degrees from orthogonality between vector E and segment $M_i$. In particular if E is orthogonal to $M_i$, then D(E, $M_i$)=0, if E is parallel to $M_i$, then D (E, $M_i$)=90°. If the value $D_{min}$ is higher than a predetermined threshold, there exists a segment in the model with suboptimal condition for 2D strain analysis. In other words, there is no a single projection for reliable strain analysis. In such a case the next type of optimization problem can be solved. Namely, $$F_{min} = F(E_{min}^1, E_{min}^2) = \min_{E^1, E^2} F(E^1, E^2) \tag{11}$$

$$F(E^1, E^2) = \max_k \min\{D(E^1, M_i), D(E^2, M_i)\}$$

Problem formulation (10)-(11) assumes that every segment will be analyzed in its preferable projection. Obviously the value $F_{min}$ is less than $D_{min}$. Optimization method is easily generalized for any number of projections.

In a case where the 3D model of the vessels is constructed from two projections, it is possible to first use these two already available projections to find segments that are viewed orthogonally in these projections. The optimization problem (9), (10), (11), can then be solved for those segments of the model that are not imaged orthogonally enough in the existing two projections.

Consolidation of 2 Motion Maps

In a case when a vessel part is observed in two different projection directions and a 3D model of the observed part is available, the two motion maps corresponding to the different projection directions can be consolidated into a single motion map. It is assumed that the 3D model for common observed in 2 projections part in every point has a reference to two matched 2D locations. Therefore the timing value in this 2D location can be defined using two values of 2D timings. The most simple naïve way of combination is average of the two numbers. A more complex definition can use direction of the 3D vessel in each location in relation to viewing direction of each projection. For example timing value from projection with more orthogonal view to the given segment can obtain greater weight than the value from less orthogonal view. In addition a combination function can incorporate some characteristics of reliability/confidence of 2D measurement: percent of contraction, quality of the fit from definition of timing value.

Some aspects of the invention are described above with reference to flowchart illustrations and/or block diagrams of methods, apparatus (systems) and computer program products according to embodiments of the subject matter. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

It will be appreciated by persons skilled in the art that the present invention is not limited to what has been particularly shown and described hereinabove. Rather the scope of the present invention is defined only by the claims which follow.

What is claimed is:

1. A method for detecting and analyzing heart mechanical activity at a region of interest of a patient's heart, comprising the following steps:
   acquiring a time sequence of 2-dimensional X-ray images of said region of interest over at least part of a cardiac cycle;
   detecting coronary vessels in said X-ray images;
   tracking the coronary vessels through said sequence of images to identify movements of the coronary vessels according to the time sequence of 2-dimensional X-ray images taken over at least part of a cardiac cycle;
   analyzing the movements of the coronary vessels to quantify at least one parameter characterizing heart wall motion in said region of interest; and
   generating a strain graph of said region of interest representing contraction or expansion or both contraction and expansion over time through said at least part of the cardiac cycle.

2. The method of claim 1, wherein said X-ray images are angiograms obtained by injection of a contrast agent.

3. The method of claim 1, wherein said X-ray images are images of a radiopaque device inserted through the coronary vessels.

4. The method of claim 1 wherein said analyzing comprises decomposing said movements into a strain component and a non-strain component.

5. The method of claim 1, wherein said analyzing comprises quantifying at least one of a strain component of motion and a displacement component of motion.

6. The method of claim 1, wherein said at least one parameter relates to at least one of a magnitude of contraction, a timing of contraction, a magnitude of displacement and a timing of displacement.

7. The method of claim 1, wherein said at least one parameter is a timing of at least one of the following: start of contraction; end of contraction; and
   a maximal velocity of contraction.

8. The method of claim 7 wherein said timing is derived from said strain graph.

9. The method of claim 8 wherein said timing is derived from said strain graph by using a curve fitting technique.

10. The method of claim 8 wherein said tracking of coronary vessels comprises calculating local transformations of the coronary vessels through said time sequence of images.

11. The method of claim 10, wherein said local transformations are decomposed into a strain component and a non-strain component and wherein said strain graph is calculated using scale factors obtained by said local transformation.

12. The method of claim 8, wherein said tracking of coronary vessels comprises selecting and tracking a plurality of control points in the coronary vessels through said time sequence of images.

13. The method of claim 12, wherein said strain graph is measured as a change in time of weighted root mean squares of distances between said control points to a mass center of said control points.

14. The method of claim 12, wherein said strain graph is measured as change in time of weighted average distances between said control points.

15. The method of claim 12, wherein said strain graph is measured as a change in time of weighted root mean squares of distances between said control points to a reference point.

16. The method of claim 1, wherein said region of interest is divided into two or more segments and wherein said analyzing comprises quantifying said at least one parameter for each of said two or more segments.

17. The method of claim 16 wherein the method further comprises generating and displaying a motion map, said motion map presents spatial distribution of values of said at least one parameter.

18. The method of claim 17 wherein said at least one parameter is timing of contraction and wherein the method further comprises identifying last to contract segment.

19. The method of claim 17, further comprising a step of identifying a location for treatment based on said motion map.

20. The method of claim 17, further comprising a step of assessing severity of a disease based on said motion map.

21. The method of claim 17 wherein said region of interest is the left ventricle and wherein the method further comprises a step of selecting a location for implanting a left ventricle pacing lead based on said motion map.

22. The method of claim 17 wherein said at least one parameter is contractility and wherein the method further comprises detecting a scar tissue based on the quantification of the contractility.

23. The method of claim 1, wherein said at least part of the cardiac cycle is a systole.

24. The method of claim 1, wherein the coronary vessels are coronary veins.

25. The method of claim 1, further comprising a step of selecting a projection direction for acquiring said time sequence.

26. The method of claim 25, wherein said projection direction is at least one of an orthogonal view to the heart's surface at the region of interest and an orthogonal view to rotational motion of the heart at the region of interest.

27. The method of claim 25, wherein said projection direction is derived from a 3D model of the coronary vessels reconstructed from two angiograms taken from different perspectives.

28. The method of claim 1 wherein the method comprises acquiring two or more time sequences of X-ray images of said region of interest under different projection directions and quantifying said at least one parameter using analysis results obtained from analyzing each of said two or more time sequences.

29. The method of claim 28 wherein motion maps obtained from analysis of said two or more time sequences are consolidated into a single motion map.

30. The method of claim 1 further comprising a step of comparing electrical activity and mechanical activity at at least one location in said region of interest.

31. The method of claim 1 further comprising a step of applying an electrical activation at at least one location in the patient's heart and wherein said acquiring of X-ray images is performed in response to said applying of electrical activation.

32. An apparatus for heart motion analysis comprising:
an image acquisition unit for receiving one or more time sequences of X-ray images exposing coronary vessels; and
a processor configured with one or more applications programs comprising computer instructions for:
identifying and tracking the coronary vessels through said one or more time sequences of images;
identifying movements of the coronary vessels according to the time sequence of 2-dimensional X-ray images taken through at least part of a cardiac cycle; and
analyzing movements of the coronary vessels and quantifying of motion of at least one region of heart;
the processor is further configured to generate local strain graphs of said region of interest representing contraction or expansion or both contraction and expansion over time through said at least part of the cardiac cycle.

33. The apparatus of claim 32 wherein the processor is further configured to generate motion maps.

34. The apparatus of claim 33 further comprising a display unit to display said strain graphs and motion maps.

35. The apparatus of claim 32 further comprising a projection direction selection unit for selecting a projection direction for capturing said one or more time sequences of X-ray images.

36. A non-transitory computer readable storage medium containing a set of instructions for a general purpose computer, the set of instructions comprising:
receiving a time sequence of 2-dimensional X-ray images of showing a region of interest over at least part of a cardiac cycle;
detecting coronary vessels in said X-ray images;
tracking the coronary vessels through said sequence of images to identify movements of the coronary vessels according to the time sequence of 2-dimensional X-ray images taken over at least part of a cardiac cycle;
analyzing the movements of said coronary vessels to obtain at least one parameter characterizing heart wall motion in said region of interest;
generating a local strain graph of said region of interest representing contraction or expansion or both contraction and expansion over time through said at least part of the cardiac cycle.

* * * * *